United States Patent [19]

Marcu

[11] Patent Number: 6,083,732
[45] Date of Patent: Jul. 4, 2000

[54] BIOLOGICALLY ACTIVE ALTERNATIVE FORM OF THE IKKAα IκB KINASE

[75] Inventor: Kenneth B. Marcu, Stony Brook, N.Y.

[73] Assignee: The Research Foundation of the State University of New York, Albany, N.Y.

[21] Appl. No.: 09/160,483

[22] Filed: Sep. 25, 1998

[51] Int. Cl.$^7$ ............... C12N 9/12; C12N 1/20; C12N 15/00; C12N 5/00; C12N 21/04
[52] U.S. Cl. ............ 435/194; 435/320.1; 435/352.3; 435/325; 536/23.2
[58] Field of Search ................ 435/194, 320.1, 435/325, 252.3; 536/23.2

[56] References Cited

U.S. PATENT DOCUMENTS

| | | | |
|---|---|---|---|
| 5,776,717 | 7/1998 | Cao | 435/15 |
| 5,804,374 | 9/1998 | Baltimore et al. | 435/6 |

OTHER PUBLICATIONS

Mock et al., "CHUK, a Conserved Helix–Loop–Helix Ubiquitous Kinase, Maps to Human Chromosome 10 and Mouse Chromosome 19", *Genomics* 27:348–351 (1995).

Margery A. Connelly and Kenneth B. Marcu, "CHUCK, a New Member of the Helix–Loop–Helix and Leucine Zipper Families of Interacting Proteins, Contains a Serine–Theronine Kinase Catalytic Domain", *Cellular and Molecular Biology Research* vol. 41:537–549 (1995).

DiDonato et al., "A Cytokine–Responsive IκB Kinase That Activates The Transcription Factor NF–κB", *Nature* 388:548–554 (1997).

Regnier et al., "Identification and Characterization of an IκB Kinase", *Cell* vol. 90:373–383 (1997).

Stancovski Ilana and David Baltimore, "NF–κB Activation: The IκB Kinase Revealed?", *Cell* 91:299–302 (1997).

Woronicz et al., "IκB Kinase–β:NF–κB Activation and Comples Formation with IκB Kinase–α and NIK", *Science* vol. 278:866–869 (1997).

Zandi et al., "The IκB Kinase Complex (IKK) Contains Two Kinase Subunits, IKKα and IKKβ, Necessary for IκB Phosphorylation and NF–κB Activation", *Cell* vol. 91: 243–252 (1997).

*Primary Examiner*—Ponnathpu Achutamurthy
*Attorney, Agent, or Firm*—Hoffmann & Baron, LLP

[57] ABSTRACT

The present invention provides an isolated IκB kinase designated IKKαΔC, that regulates NFκB gene transcription. IKKαΔC is an IκB protein kinase having a kinase domain, a leucine zipper like α-helix domain, and no helix-loop-helix domain. Also provided are the amino acid sequence of IKKαΔC, the nucleotide sequence encoding IKKαΔC, and other related protein and nucleic acid molecules. The invention provides antibodies specific for IKKαΔC and methods of using the IKKαΔC proteins of the invention in the development of antiinflammatory agents or immunosuppressants.

8 Claims, 8 Drawing Sheets

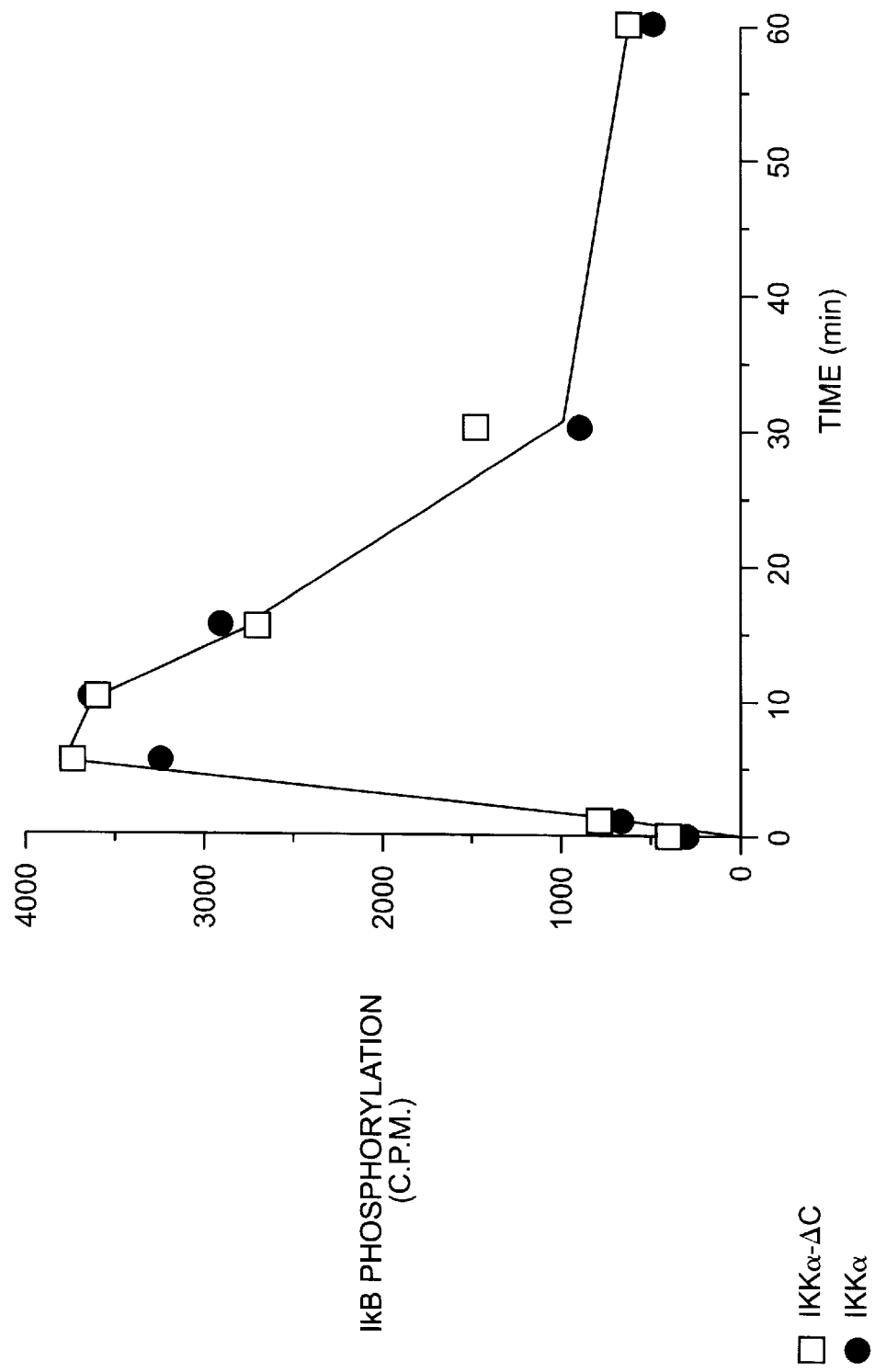

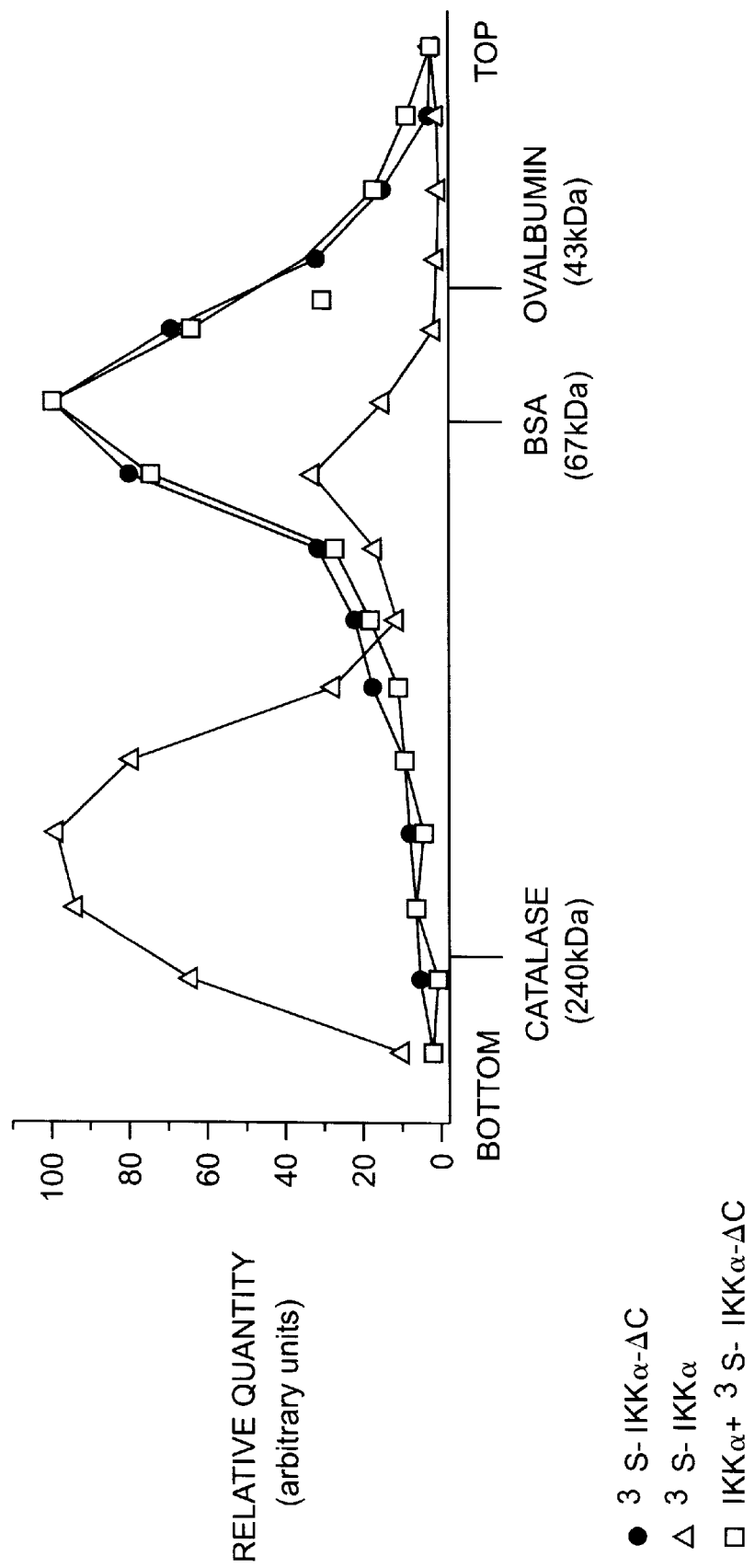
FIG. 4A IKKα AND IKKα-ΔC

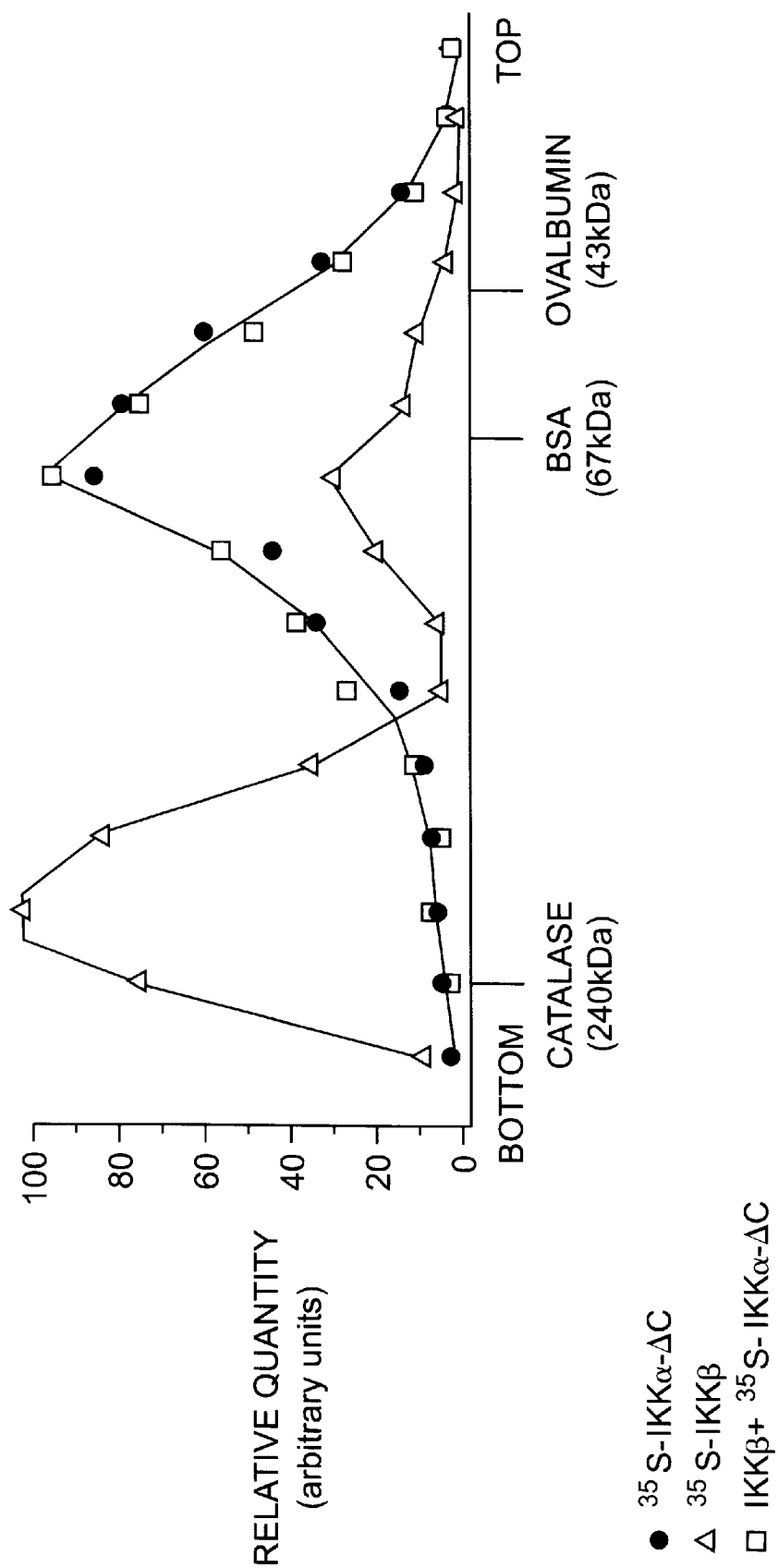

6,083,732

SEQUENCE LISTING

<160> NUMBER OF SEQ ID NOS: 3

<210> SEQ ID NO 1
<211> LENGTH: 584
<212> TYPE: PRT
<213> ORGANISM: mus.musculus domesticus

<400> SEQUENCE: 1

```
Met Glu Arg Pro Pro Gly Leu Arg Pro Gly Ala Gly Gly Pro Trp Glu
  1               5                  10                  15

Met Arg Glu Arg Leu Gly Thr Gly Gly Phe Gly Asn Val Ser Leu Tyr
                 20                  25                  30

Gln His Arg Glu Leu Asp Leu Lys Ile Ala Ile Lys Ser Cys Arg Leu
             35                  40                  45

Glu Leu Ser Ser Lys Asn Arg Glu Arg Trp Cys His Glu Ile Gln Ile
         50                  55                  60

Met Lys Lys Leu Asp His Ala Asn Val Val Lys Ala Cys Asp Val Pro
     65                  70                  75                  80

Glu Glu Leu Asn Phe Leu Ile Asn Asp Val Pro Leu Leu Ala Met Glu
                 85                  90                  95

Tyr Cys Ser Gly Gly Asp Leu Arg Lys Leu Leu Asn Lys Pro Glu Asn
                100                 105                 110

Cys Cys Gly Leu Lys Glu Ser Gln Ile Leu Ser Leu Leu Ser Asp Ile
            115                 120                 125

Gly Ser Gly Ile Arg Tyr Leu His Glu Asn Lys Ile Ile His Arg Asp
        130                 135                 140

Leu Lys Pro Glu Asn Ile Val Leu Gln Asp Val Gly Gly Lys Thr Ile
145                 150                 155                 160

His Lys Ile Ile Asp Leu Gly Tyr Ala Lys Asp Val Asp Gln Gly Ser
                165                 170                 175

Leu Cys Thr Ser Phe Val Gly Thr Leu Gln Tyr Leu Ala Pro Glu Leu
            180                 185                 190
```

```
Phe Glu Asn Lys Pro Tyr Thr Ala Thr Val Asp Tyr Trp Ser Phe Gly
            195                 200                 205

Thr Met Val Phe Glu Cys Ile Ala Gly Tyr Arg Pro Phe Leu His His
210                 215                 220

Leu Gln Pro Phe Thr Trp His Glu Lys Ile Lys Lys Asp Pro Lys
225                 230                 235                 240

Cys Ile Phe Ala Cys Glu Met Thr Gly Glu Val Arg Phe Ser Ser
                245                 250                 255

His Leu Pro Gln Pro Asn Ser Leu Cys Ser Leu Ile Val Glu Pro Met
            260                 265                 270

Glu Ser Trp Leu Gln Leu Met Leu Asn Trp Asp Pro Gln Gln Arg Gly
            275                 280                 285

Gly Pro Ile Asp Leu Thr Leu Lys Gln Pro Arg Cys Phe Ala Leu Met
290                 295                 300

Asp His Ile Leu Asn Leu Lys Ile Val His Ile Leu Asn Met Thr Ser
305                 310                 315                 320

Ala Lys Ile Ile Ser Phe Leu Leu Pro Cys Asp Glu Ser Leu His Ser
                325                 330                 335

Leu Gln Ser Arg Ile Glu Arg Glu Thr Gly Ile Asn Thr Gly Ser Gln
            340                 345                 350

Glu Leu Leu Ser Glu Thr Gly Ile Ser Leu Asp Pro Arg Lys Pro Ala
            355                 360                 365

Ser Gln Cys Val Leu Asp Gly Val Arg Gly Cys Asp Ser Tyr Met Val
            370                 375                 380

Tyr Leu Phe Asp Lys Ser Lys Thr Val Tyr Glu Gly Pro Phe Ala Ser
385                 390                 395                 400

Arg Ser Leu Ser Asp Cys Val Asn Tyr Ile Val Gln Asp Ser Lys Ile
                405                 410                 415

Gln Leu Pro Ile Ile Gln Leu Arg Lys Val Trp Ala Glu Ala Val His
            420                 425                 430

Tyr Val Ser Gly Leu Lys Glu Asp Tyr Ser Arg Leu Phe Gln Gly Gln
            435                 440                 445

Arg Ala Ala Met Leu Ser Leu Leu Arg Tyr Asn Ala Asn Leu Thr Lys
450                 455                 460

Met Lys Asn Thr Leu Ile Ser Ala Ser Gln Gln Leu Lys Ala Lys Leu
465                 470                 475                 480

Glu Phe Phe Arg Lys Ser Ile Gln Leu Asp Leu Glu Arg Tyr Ser Glu
                485                 490                 495

Gln Met Thr Tyr Gly Ile Ser Ser Glu Lys Met Leu Lys Ala Trp Lys
            500                 505                 510

Glu Met Glu Glu Lys Ala Ile His Tyr Ser Glu Val Gly Val Ile Gly
            515                 520                 525

Tyr Leu Glu Asp Gln Ile Met Ser Leu His Thr Glu Ile Met Glu Leu
            530                 535                 540

Gln Lys Ser Pro Tyr Gly Arg Arg Gln Gly Asp Leu Met Glu Ser Leu
545                 550                 555                 560

Glu Gln Arg Ala Ile Asp Leu Tyr Lys Gln Leu Lys His Arg Pro Pro
                565                 570                 575

Gly Lys Thr Leu Gln Ser Gln Tyr
            580

<210> SEQ ID NO 2
<211> LENGTH: 2025
```

```
<212> TYPE: DNA
<213> ORGANISM: mus.musculus domesticus

<400> SEQUENCE: 2
gggaccggcc ttagaccggc ggcgttgcct gaggcggctg gcgctcccgc cccatggagc      60
ggccccgggg gctgcggccg ggcgcgggcg gccctggga gatgcgggaa cggcttggca     120
ccggcggttt cgggaacgtc agtctgtacc agcaccggga acttgatctc aaaatagcaa     180
ttaagtcttg tcgtttagag ctaagttcca aaaacagaga gcgatggtgc catgaaatcc     240
agatcatgaa aaagttggac catgcgaatg ttgtaaaggc ctgtgatgtc cctgaggaat     300
tgaactttt aattaacgat gtgcctcttc tggcaatgga gtactgttct ggaggggacc     360
tccggaagct actcaacaaa ccagaaaatt gttgtggact aaagaaagc cagatacttt     420
ctttactgag tgacatagga tctgggatcc gatatctgca tgaaaacaaa attatacatc     480
gagatctaaa acctgaaaat atagttcttc aagatgttgg tgggaagaca atacataaaa     540
taattgattt gggttatgcc aaagatgttg atcaaggaag tctctgtaca tcttttgtgg     600
gaacattgca gtatttggcc ccagagctct ttgaaaataa gccgtacaca gccactgtgg     660
attattggag ctttgggacc atggtgtttg aatgtattgc tggatatagg cctttttttgc     720
atcatctgca gccatttacc tggcatgaga agattaagaa gaaagatcca aagtgtatat     780
ttgcatgtga agagatgact ggagaagttc ggtttagtag ccatttacct cagccaaaca     840
gcctttgtag tttaatagta gagccaatgg aaagctggct ccaattgatg ctgaattggg     900
acccacagca gagaggggga cctattgatc ttactttgaa gcagccaaga tgttttgcat     960
taatggatca cattctcaat ttaaagatag tgcacatcct aaatatgact tctgcaaaaa    1020
tcatttctt tctgttacca tgtgatgaaa gtcttcattc actacagtct cgaattgagc    1080
gtgaaacagg aataaataca ggttctcagg agcttctgtc agagacaggg atttctctgg    1140
atcctcggaa accagcctct cagtgtgttc tagatggagt tagaggctgt gatagctaca    1200
tggtttattt gtttgataaa agtaagactg tatatgaagg accatttgca tccagaagtt    1260
tatctgattg tgtaaattat attgtacaag acagcaaaat acaactgcca attatacagc    1320
tgcggaaagt atgggctgaa gcagtgcact acgtatctgg gctaaaggaa gactacagca    1380
ggctcttcca gggacaaaga gcagcaatgt taagtcttct tagatataat gctaacttga    1440
caaaaatgaa gaatactttg atctcagcat cacagcaact caaagctaaa ttggagtttt    1500
ttcgaaaaag cattcagctt gacttggaga gatatagtga gcagatgact tatgggatat    1560
cttcagaaaa aatgttaaaa gcatggaaag aaatggaaga aaaggccatt cactattctg    1620
aggttggtgt cattggttat cttgaggatc aaattatgtc tttgcacact gaaatcatgg    1680
agctgcagaa gagcccctac ggacgacgcc agggagactt gatggagtct ctggagcagc    1740
gtgccattga tctctataag cagctaaagc acagacctcc tggtaagaca cttcagtcac    1800
agtattgaaa ggtggtttag gaaacaccct aactgaacaa agtgggtaaa ttttaatgtt    1860
ttttaacttc atagtatgat cctgtttttgg tattcttttt gcaacatttg tggcataata    1920
gctttaaatt tataaaaact taaagatta gaagaggaag taataaggat attgaagtag    1980
aaaagttta aaagtgaagt gaaaagaaag tagagaagaa aaaaa                    2025

<210> SEQ ID NO 3
<211> LENGTH: 8
<212> TYPE: PRT
<213> ORGANISM: mus.musculus domesticus
```

-continued

```
<400> SEQUENCE: 3

Gly Lys Thr Leu Gln Ser Gln Tyr
 1               5
```

BIOLOGICALLY ACTIVE ALTERNATIVE FORM OF THE IKKAα IκB KINASE

This invention was made with governmental support under Grant No. CA36246 sponsored by the National Cancer Institute of the National Institutes of Health. The government has certain rights in this invention.

BACKGROUND OF THE INVENTION

The NF-κB family of transcription factors are involved in the regulation of a wide variety of cellular responses. These transcription factors mediate extracellular signals that induce expression of genes which are involved in such diverse processes as cell division, inflammation, and apoptosis. See, for example, Baldwin, Annu.Rev. Immunol. 12, 141–179 (1996); Beg and Baltimore, Science 274, 782–274 (1996); Gilmore et al., Oncogene 13, 1267–1378 (1996); Mayo, et al, Science 278, 1812–1815 (1997); and Van Antwerp et al., Science 274, 787–789 (1996).

NF-κB is anchored in the cytoplasm of most non-stimulated cells by a non-covalent interaction with one of several inhibitory proteins known as IκBs. See for example, Baeuerle and Baltimore, Science 242, 540–546 (1988). Cellular stimuli associated with immune and inflammatory responses, for example inflammatory cytokines such as tumor necrosis factor α (TNFα) or interleukin-1 (IL-1), activate NF-κB by inducing the phosphorylation of IκBs on specific serine residues. Phosphorylation marks the IκBs for ubiquitination and proteosome mediated degradation. The disruption, or dissociation, of IκBs from NF-κB unmasks the NF-κB nuclear localization signal, and facilitates the nuclear translocation of active NF-κB to the nucleus, thereby upregulating NF-κB responsive target genes. See, for example, Baeuerle and Henkel, Annu. Rev. Immunol., 12, 141–179 (1994); Baldwin, Annu.Rev. Immunol., 14, 649–683 (1996); Siebenlist et al., Annu.Rev.Cell Biol. 12, 405–455 (1994); and Verma et al, Genes Dev., 9, 2723–2735 (1995). Thus, this phosphorylation of IκBs is a key regulatory step for NF-κB mediated processes.

Phosphorylation of IκBs on two amino proximal serine residues (for example, in the case of IκBα serines 32 and 36) has long been appreciated to be the major regulatory step in NF-κB activation. See, for example, Baldwin, Annu.Rev. Immunol., 14, 649–683 (1996), Brown et al., Science 267, 1485–1488 (1995); DiDonato et al., Mol. Cell Biol. 16, 1295–1304 (1996); Traenckner et al., EMBO J., 14, 2876–2883 (1995). As such, an important key to elucidating the mechanism of NF-κB activation, and gaining control of the immune and inflammatory responses mediated by NF-κB activation, is determining the kinases involved.

Therefore, there is a need for finding kinases that are involved in the regulation of these processes. Initial attempts to identify the responsible kinase(s) revealed a specific IκB-kinase activity in a large, around 700 kDa, cytoplasmic complex. Chen et al., Genes Dev. 9, 1586–1597 (1995). The activation of this kinase can be mediated by mitogen-activated protein kinase kinase kinase-1 (MEKK-1), although the precise mechanism has not yet been established. Lee et al., Cell 88, 213–222 (1997).

Further experiments to decipher the functional connection between TRAFs (TNF-receptor-associated factors) and NF-κB activation led to the isolation of NF-κB-inducing kinase (NIK). Lee et al., Cell 88, 213–222 (1997); and Malinin et al., Nature 385, 540–544 (1997). NIK is a serine/threonine kinase which shares homology to MEKK-1. Phosphorylation of IκB in response to TNFα requires NIK function. Lee et al., Cell 88, 213–222 (1997); and Malinin et al., Nature 385, 540–544 (1997); Song et al. Proc. Natl.Acad.Sci 94, 9792–9796 (1997). However, NIK does not directly phosphorylate NF-κB. Lee et al., Cell 88, 213–222 (1997).

Of critical importance for elucidating, and controlling, the signaling pathways that lead to NF-κB activation is the determination and characterization of kinases that directly phosphorylate IκB. The abbreviation "IKK" is used to designate an IκB kinase. Recently, an IκB kinase (IKK), designated IKKα, was identified in a yeast-two-hybrid screen with NIK as bait. Regnier et al., Cell 90, 373–383 (1997). IKKα was also purified using conventional biochemical techniques and determined to be the major IκB kinase activity induced by TNF stimulation of HeLa cells. DiDonato et al., Nature 388, 548–554 (1997). IKKα had been cloned previously in a reverse transcriptase polymerase chain reaction (RT-PCR) based search for myc-like genes containing helix-loop-helix domains and was termed CHUK (conserved helix-loop-helix ubiquitous kinase). Connelly and Marcu, Cellular and Molecular Biology Research 41, 537–549 (1995). CHUK was renamed IKKα when its function was discovered. Regnier et al. (1997). The identification of IKKα (CHUK) as a cytoplasmic kinase which phosphorylates IκB family members at their physiologically relevant sites and targets them for proteosome-mediated degradation was a major breakthrough.

The IKKα (CHUK) gene encodes a 745 amino-acid polypeptide (having a molecular mass of approximately 85 kDa). Murine and human IKKα (CHUK) cDNA clones were found to be almost identical. Connelly and Marcu, Cellular and Molecular Biology Research 41, 537–549 (1995). Another kinase, termed IKKβ, homologous to IKKα, has also been reported. Stancovski and Baltimore, Cell 91, 299–302 (1997); Woronicz et al., Science 278, 866–869 (1997); and Zandi et al. Cell 91, 243–252 (1997). IKKα and IKKβ have 52% overall similarity to each other and 65% identity in the kinase domain. Zandi et al., Cell 91, 243–252 (1997). An IκB kinase termed T2K has also been described in U.S. Pat. No. 5,776,717 to Cao.

The known IκB protein kinases generally phosphorylate IκBs at specific serine residues. They specifically phosphorylate serines 32 and 36 of IκBα. Phosphorylation of both sites is required to efficiently target IκBα for destruction in vivo. Moreover, activation of IKKα and IKKβ occurs in response to NF-κB activating agents and mutant IKKα and IKKβ that are catalytically inactive block NF-κB stimulation by cytokines. These results highlight the important role played by IκB protein kinases in NF-κB activation processes. See Stancovski and Baltimore, Cell 91, 299–302 (1997) for a recent discussion of IκB kinases.

IKKα (CHUK) and IKKβ have structural motifs characteristic of the IKK-kinases. This includes an amino terminal serine-threonine kinase domain separated from a carboxyl proximal helix-loop-helix (H-L-H) domain by a leucine zipper-like amphipathic α-helix structure. These structural characteristics are unlike other kinases and the domains are thought to be involved in protein-protein interactions.

The discovery of IKK kinases will facilitate elucidation of the events triggered by the engagement of cytokine receptors which lead to the activation of the cytoplasmically anchored NF-κB transcription factors. This is of great importance because NF-κB gene regulation is involved in a host of pathological events, in addition to inflammatory processes. For example, NF-κB gene regulation has been implicated in the progression of acquired immune deficiency syndrome (AIDS), acute phase response, activation of immune and endothelial cells during toxic shock, allograft rejection, and radiation responses. Knowledge of the mechanisms of NF-κB activation will be invaluable in the development of therapeutic agents for these conditions.

Significantly, the discovery of kinases that are involved in activating NF-κB by phosphorylating IκBs is critical for developing means for controlling cellular processes regulated by NF-κB. In particular, there is a need for inhibitors of IκB phosphorylation that can be used to control undesirable inflammation and immune responses. Protein kinases that act at the key regulatory step of NF-κB activation provide targets for the development of inhibitors of such responses. Discovery of additional kinases involved in the phosphorylation of IκBs would aid in the rational development of means for controlling cellular processes regulated by the NF-κB system. Thus, there is a great need for the identification and characterizing of kinases that phosphorylate IκB.

SUMMARY OF THE INVENTION

The present invention provides an isolated IκB protein kinase having a kinase domain, a leucine zipper like α-helix domain, and no helix-loop-helix domain (IKKαΔC). A preferred embodiment of the invention is an isolated protein having the amino acid sequence set forth in SEQ ID NO:1. Also included are isolated nucleic acid molecules that encode the IκB protein kinase having a kinase domain, a leucine zipper like α-helix domain, and no helix-loop-helix domain. Methods of making IKKαΔC by expressing nucleic acid molecules encoding the protein are also provided. Antibodies directed to IKKαΔC are also included in the invention.

The invention also includes a method of screening for an agent which modulates IκB phosphorylation by an IκB protein kinase having a kinase domain, a leucine zipper like α-helix domain, and no helix-loop-helix domain (IKKαΔC), the method comprising the steps of:

incubating a mixture comprising:
        the IκB protein kinase having a kinase domain, a leucine zipper like α-helix domain, and no helix-loop-helix domain (IKKαΔC),
        an IκB phosphorylation site, and
        a candidate modulating agent;
    detecting an agent-biased phosphorylation level of the phosphorylation site by the kinase;
    comparing the agent-biased phosphorylation level with an agent-independent phosphorylation level determined in the absence of the modulating agent;
    wherein a substantial difference between the agent-biased phosphorylation level and the agent-independent phosphorylation level indicates that the agent modulates IκB phosphorylation.

DESCRIPTION OF THE FIGURES

FIG. 3 shows time course experiments of IκB phosphorylation by IKKα and IKKαΔC.

FIGS. 4A and 4B show that IKKαΔC is a monomer.

DETAILED DESCRIPTION OF THE INVENTION

Figure 1A:
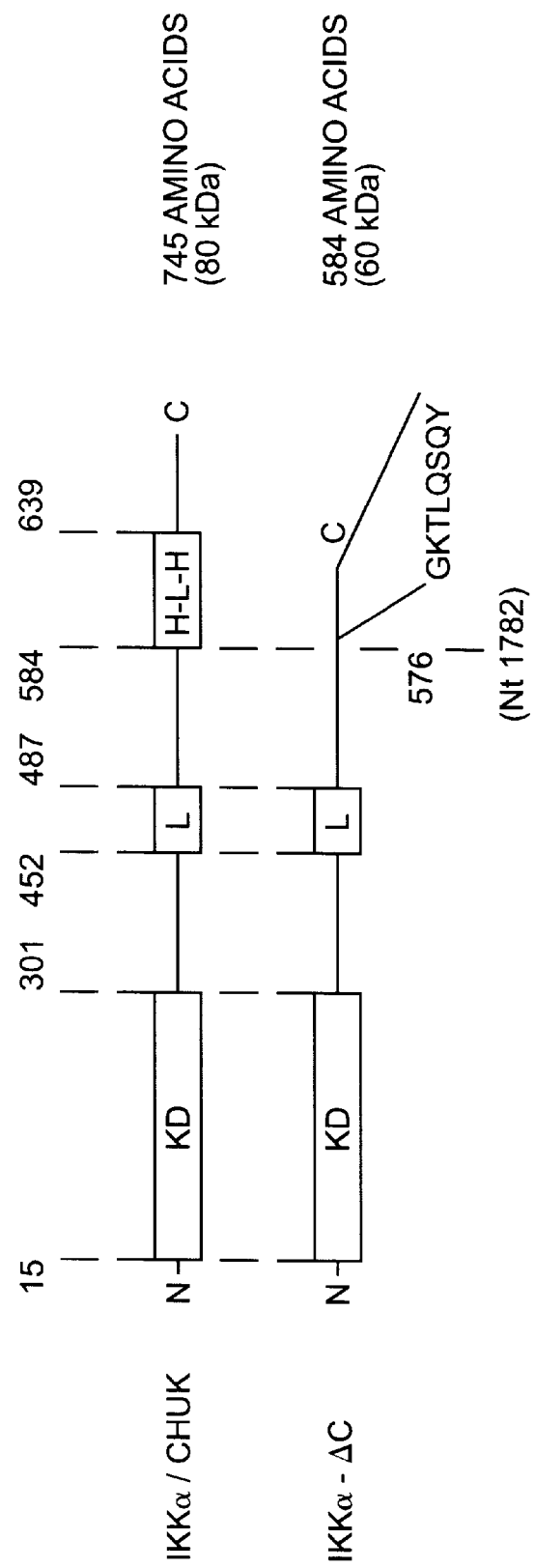
FIG. 1A is a schematic representation that compares the domain structures of murine IKKα and murine IKKαΔC.
Figure 1B:
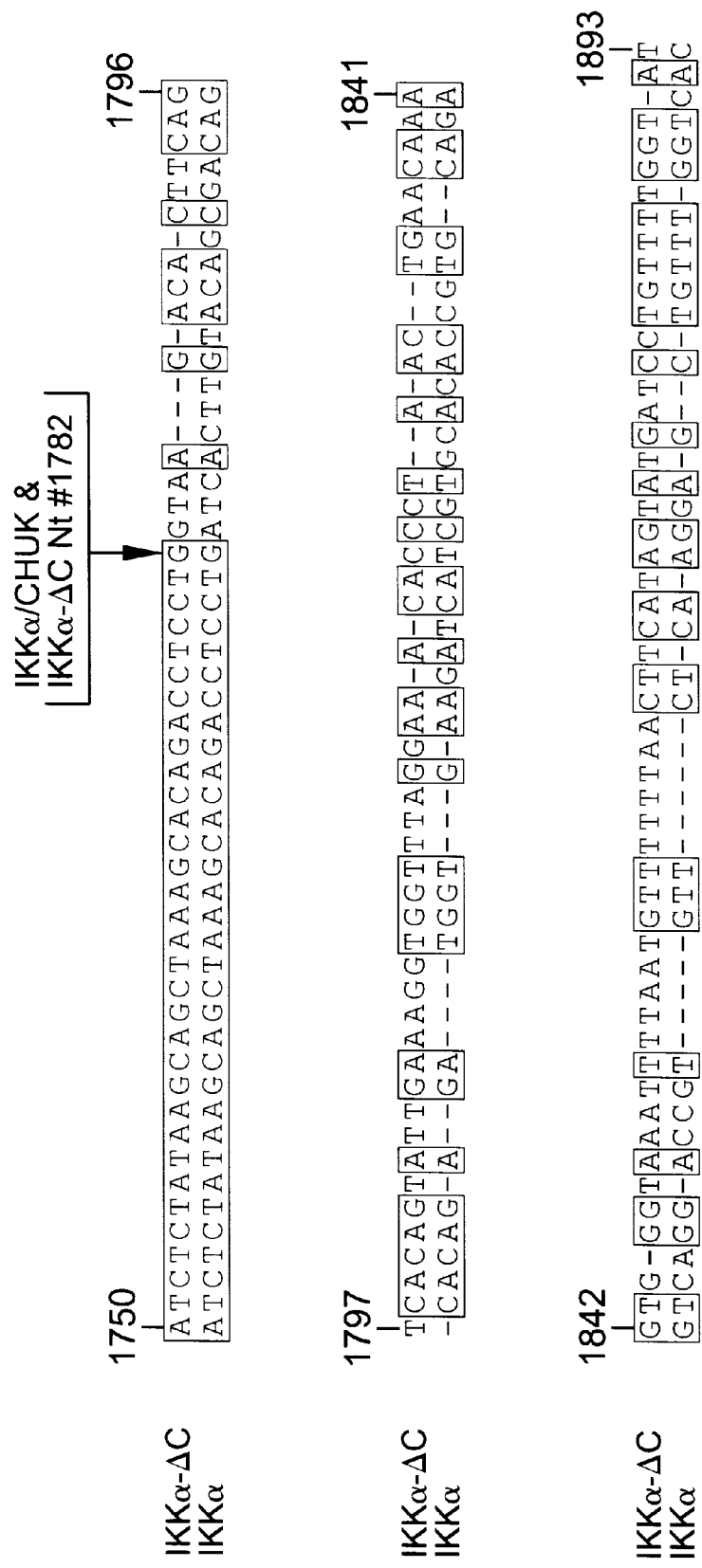
FIG. 1B is a nucleotide sequence alignment of IKKαΔC and IKKα at the point of their divergence.

The invention is directed to an IκB protein kinase, designated IKKαΔC, which is a previously unknown cellular isoform of IKKα. A comparison of the domain structures of murine IKKαΔC and murine IKKα is shown in FIG. 1. IKKαΔC shares a similar primary structure to IKKα from the N-terminal region through amino acid 576 (Oust prior to the helix-loop-helix domain of IKKα) whereupon IKKαΔC diverges. IKKαΔC differs from other known IκB kinases because it lacks the carboxyl terminal helix-loop-helix domain. IKKαΔC is a polypeptide of about 60 kDa, and as shown in FIG. 1A, the kinase domain (KD) and leucine zipper (LZ) domains of IKKαΔC are similar to IKKα. The kinase domain of these proteins comprises a region from about amino acid 15 to about amino acid 301 and the leucine zipper region comprises a region from about amino acid 452 to about amino acid 487.

Protein kinases are enzymes that phosphorylate proteins at defined locations. The sites of phosphorylation are usually the hydroxyl groups of Ser and Thr amino acid residues, although Tyr, His, and Lys can also be phosphorylated depending on the kinase and the structure of the substrate protein. Leucine zipper and helix-loop-helix domains were hitherto known as common structural motifs found in proteins that bind DNA. These domains typically have an amphipathic character.

IKKαΔC is a functional IκB kinase that responds to inflammatory cytokines as a monomeric protein. Because of its novel structure and capacity to act as a monomer, IKKαΔC provides a unique target for the development of inhibitors of IκB phosphorylation and for obtaining anti-inflammatory therapeutics.

Mutations in the helix-loop-helix domain greatly decrease kinase activity and it is believed that the helix-loop-helix domain plays a critical role in the proper structural orientation of the protein required for functionality. Therefore, it was unexpected that an IκB kinase without the helix-loop-helix domain would be functional.

Moreover, IKKα and IKKβ function as a complex. Therefore, it was unexpected that IKKαΔC is a cytokine-inducible IκB kinase that does not associate with either IKKα or IKKβ. Unlike known IκB kinases, IKKαΔC can act as a functional monomer.

Even more surprising was the inventor's discovery that IKKαΔC was more potent at upregulating NF-κB in response to cytokine stimulation than known IκB kinases such as IKKα. This was a highly unexpected finding because IKKα and IKKβ were believed to be crucial for IκB phosphorylation. Therefore, the participation of an alternative form of IKK was unexpected.

In a first embodiment, the invention provides an isolated IκB protein kinase (IKKαΔC) having a kinase domain, a leucine zipper like α-helix domain, and unlike other IKK kinases, no helix-loop-helix domain. As long as IκB kinase function is maintained, IKKαΔC may have any kinase domain, any leucine zipper domain, and either any carboxyl-terminal domain that is not a Helix-Loop-Helix domain or no carboxyl-terminal domain.

In one embodiment of the invention, the kinase domain is a Serine/Threonine kinase domain. In another embodiment of the invention, the carboxyl-terminal region comprises the amino acid sequence GKTLQSQY set forth in SEQ ID NO:3. In yet another embodiment, the invention provides an IKKαΔC polypeptide having the amino sequence set forth in SEQ ID NO:1.

The invention further includes minor modifications, and all naturally occurring alleles, of the polypeptide set forth in SEQ ID NO:1 that result in proteins which have substantially equivalent activity. Modifications may be deliberate, as by site-directed mutagenesis, or may be spontaneous mutations. Alleles may be from any species. The invention includes all of these polypeptides so long as IKKαΔC activity is retained.

For example, the invention also includes conservative variations or equivalent variants of SEQ ID NO:1. The terms "conservative variation" and "equivalent variant" as used herein denote the replacement of amino acids by other amino acids that have similar chemical and biological properties, or that are generally considered equivalent.

For example, it is known in the art to substitute amino acids in a sequence with equivalent amino acids, i.e. conservative variations. Groups of amino acids normally considered to be equivalent are:

(a) Ala (A), Ser (S), Thr (T), Pro (P), Gly (G);
(b) Asn (N), Asp (D), Glu (E), Gln (Q);
(c) His (H), Arg (R), Lys (K);
(d) Met (M), Leu (L), Ile (I), Val (V); and
(e) Phe (F), Tyr (Y), Trp (W).

Substitutions, additions, and/or deletions in the protein sequences may be made as long as the function of the proteins of the invention is maintained. Equivalent proteins will normally have substantially the same amino acid sequence as the native proteins. An amino acid sequence that is substantially the same as another sequence, but that differs from the other sequence by means of one or more substitutions, additions and/or deletions, is considered to be an equivalent sequence, equivalent variant or conservative variation. Preferably, less than 25%, more preferably less than 10%, of the number of amino acid residues in a sequence are substituted for, added to, or deleted from the proteins of the invention.

The proteins of the invention are isolated. The term "isolated" as used herein, in the context of proteins, refers to an IKKαΔC polypeptide which is unaccompanied by at least some of the material with which it is associated in its natural state. The isolated protein constitutes at least 0.5%, preferably at least 5%, more preferably at least 25% and still more preferably at least 50% by weight of the total protein in a given sample. Most preferably the "isolated" protein is substantially free of other proteins, lipids, carbohydrates or other materials with which it is naturally associated, and yields a single major band on a non-reducing polyacrylamide gel.

The invention also provides isolated nucleic acid molecules that encode IKKαΔC and the variants of these proteins described herein. The invention includes an isolated nucleic acid molecule as set forth in SEQ ID NO:2, isolated nucleic acid molecules that are substantially homologous with SEQ ID NO:2, and isolated nucleic acid molecules that hybridize with SEQ ID NO:2 under high stringent conditions.

Nucleic acid molecules (nucleic acids) of the invention include deoxyribonucleic acid (DNA), complementary DNA (cDNA), and ribonucleic acid (RNA) sequences that encode an IKKαΔC protein, or a unique fragment thereof. Such nucleic acids include naturally occurring, synthetic, and intentionally manipulated nucleic acid molecules. For example, the IKKαΔC polynucleotide sequence may be subjected to site-directed mutagenesis.

Fragments include primers and probes which are useful as tools in molecular biology and biotechnology. For example, the fragment can be used as a primer ('amplimer") to selectively amplify nucleic acid, such as genomic DNA or total RNA. Primers can also be used in nucleic acid amplification procedures such as the polymerase chain reaction (PCR), ligase chain reaction (LCR), Repair Chain Reaction (RCR), PCR oligonucleotide ligation assay (PCR-OLA), and the like.

The fragment can also be an oligonucleotide complementary to a target nucleic acid molecule, i.e., the fragment can be a probe. Such oligonucleotides can be DNA or RNA. Oligonucleotides useful as probes in hybridization studies, such as in situ hybridization, can also be constructed.

The length of the oligonucleotide probe is not critical, as long as it is capable of hybridizing to the target molecule. The oligonucleotide should contain at least 6 nucleotides, preferably at least 10 nucleotides, and more preferably, at least 15 nucleotides. There is no upper limit to the length of the oligonucleotide probes. Longer probes are more difficult to prepare and require longer hybridization times. Therefore, the probe should not be longer than necessary. Normally, the oligonucleotide probe will not contain more than 50 nucleotides, preferably not more than 40 nucleotides, and, more preferably, not more than 30 nucleotides.

Numerous methods for detectably labeling such probes with radioisotopes, fluorescent tags, enzymes, binding moieties (e.g., biotin), and the like are known, so that the probes of the invention can be adapted for easy detectability. Methods for making and using nucleic acid probes are understood by those skilled in the art. See, for example, Keller G H and Manak M M, *DNA Probes,* 2d ed., Macmillan Publishers Ltd., England (1991) and Hames B D and Higgins S J, eds., *Gene Probes I* and *Gene Probes II,* IRL Press, Oxford (1995).

Antisense nucleic acid sequences and nucleic acid sequences that are degenerate as a result of the genetic code are also within the scope of the invention. There are 20 natural amino acids, most of which are specified by more than one codon. Therefore, all degenerate nucleotide sequences are included in the invention as long as the amino acid sequence of the IKKαΔC polypeptide encoded by the sequence is functional, i.e. phosphorylates IκB. Thus, the invention also includes all nucleic acid molecules that encode a polypeptide having an amino acid sequence as set forth in SEQ ID NO:1.

The nucleic acid molecules are of synthetic (non-natural) sequences and/or they are isolated. The term "isolated," as used herein, in the context of nucleic acids, includes nucleic acid molecules unaccompanied by at least some of the material with which they are associated in their natural state. The isolated nucleic acid constitutes at least 0.5%, preferably at least 5%, more preferably at least 25% and still more preferably at least 50% by weight of the total nucleic acid in a given sample. Most preferably the "isolated" nucleic acid is substantially free of other nucleic acids, proteins, lipids, carbohydrates or other materials with which it is naturally associated. The nucleic acid molecules of the invention can also be recombinant, meaning that they comprise a non-natural sequence or a natural sequence joined to nucleotide (s) other than than those in which they are joined on the natural chromosome.

Proteins and nucleic acid molecules homologous and substantially homologous to SEQ ID NO:1 and SEQ ID NO:2 respectively are also included in the invention. In the present specification, the sequence of a first protein, protein domain, or nucleic acid, is considered homologous to a second protein, protein domain or nucleic acid if the amino acid or nucleotide sequence of the first protein, protein domain, or nucleic acid molecule is at least about 30% homologous (identical), preferably at least about 50% homologous (identical), and more preferably at least about 65% homologous (identical) to the respective sequences of the second protein, protein domain, or nucleic acid molecule.

In accordance with the present invention, substantantially homologous proteins, protein domains, or nucleic acids have sequences, either amino acid or nucleic acid sequences, that are at least about 75% homologous (identical), preferably at least about 85% homologous (identical) and, more preferably, at least about 95% homologous (identical).

Determinations of whether two amino acid sequences are substantially homologous can be, for the purpose of the present specification, based on FastA method in accordance with Pearson and Lipman, Proc. Natl. Acad. Sci. U.S.A. 85:2444–2448 (1988), or based on the FastDB method in accordance with Current Methods in Sequence Comparison and Analysis, "Macromolecular Sequencing and Synthesis, Selected Methods and Applications," pp 127–149, 1988, Alan R. Liss, Inc., using the following parameters:

Mismatch Penalty: 1.00
Gap Penalty: 1.00
Gap Size Penalty: 0.33
Joining Penalty: 30.0

The invention fragments nucleic acids that hybridize to SEQ ID NO:2, a fragment of SEQ ID NO:2, a complement of SEQ ID NO:2, or a complement of a fragment of SEQ ID NO:2 under high stringent conditions. Also included in the invention are proteins that are encoded by nucleic acid molecules that hybridize under high stringent conditions to a sequence complementary to SEQ ID NO:2.

The term "stringent conditions," as used herein, is equivalent to "high stringent conditions" and "high stringency." These terms are used interchangeably in the art.

High stringent conditions are defined in a number of ways. In one definition, stringent conditions are selected to be about 50° C. lower than the thermal melting point ($T_m$) for a specific sequence at a defined ionic strength and pH. The $T_m$ is the temperature (under defined ionic strength and pH) at which 50% of the target sequence hybridizes to a perfectly matched sequence. Typical stringent conditions are those in which the salt concentration is at least about 0.02 M at pH 7 and the temperature is at least about 60° C.

"Stringent conditions," in referring to homology or substantial similiarity in the hybridization context, can be combined conditions of salt, temperature, organic solvents or other parameters that are typically known to control hybridization reactions. The combination of parameters is more important than the measure of any single parameter. If incompletely complementary sequences recognize each other under high stringency conditions, then these sequences hybridize under conditions of high stringency. See U.S. Pat. No. 5,786,210; Wetmur and Davidson J. Mol. Biol. 31, 349–370 (1968). Control of hybridization conditions, and the relationships between hybridization conditions and degree of homology are understood by those skilled in the art. See, e.g., Sambrook J, Fritsch E F, and Maniatis T, Molecular Cloning. A Laboratory Manual, 2d ed., Cold Spring Harbor Laboratory, Cold Spring Harbor (1989).

Further examples of stringent conditions can be found in U.S. Pat. No. 5,789,550 to Goeddel et al. (1998). The description of stringent conditions in U.S. Pat. No. 5,789,550 is herein incorporated by reference. "Stringent conditions" can be provided in a variety of ways such as overnight incubation at 42° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA. Alternatively, the stringent conditions are characterized by a hybridization buffer comprising 30% formamide in 5×SSPE (0.18 M NaCl, 0.01 M NaPO$_4$, pH 7.7, 0.0001 M EDTA) buffer at a temperature of 42° C., and subsequent washing at 42° C. with 0.2×SSPE. Preferably, stringent conditions involve the use of a hybridization buffer comprising 50% formamide in 5×SSPE at a temperature of 42° C. and washing at the same temperature with 0.2×SSPE. Other stringent conditions known in the art can also be used.

IKKαΔC activity or function can be determined by assays well known in the art. A kinase assay using Glutathione S-transferase-IκB (1–62) as a substrate is described below. Glutathione S-transferase-IκB (1–62) is a recombinant fusion protein containing a 62 amino acid N-terminal fragment of IκBα. The IκBα (1–62) fragment only contains two phophoaccepting serines at positions 32 and 36. Other suitable assays are described, for example, in U.S. Pat. No. 5,776,717 to Cao. The description of IκB kinase assays in U.S. Pat. No. 5,776,717 is herein incorporated by reference.

The proteins and variants of the proteins can be prepared by methods known in the art. Such methods include isolating the protein directly from cells, and synthesizing the protein chemically from individual amino acids. Preferably, the proteins of the invention can be prepared by providing DNA that encodes the protein, amplifying or cloning the DNA, expressing the DNA in a suitable host, and harvesting the protein.

DNA encoding the proteins of the invention can be synthesized or isolated. The DNA of the invention can be synthesized chemically from the four nucleotides in whole or in part by methods known in the art. Such methods include those described by Caruthers M H, Science 230:281–285 (1985). DNA can also be synthesized by preparing overlapping double-stranded oligonucleotides, filling in the gaps, and ligating the ends together. See, generally, Sambrook et al. (1989) and Glover D M and Hames B D, eds., *DNA Cloning*, 2d ed., Vols. 1–4, IRL Press, Oxford (1995).

DNA expressing functional homologs of the protein can be prepared from wild-type DNA by site-directed mutagenesis. See, for example, Zoller and Smith, Nucleic Acids Res 10:6487–6500 (1982); Zoller, Methods Enzymol 100:468–500 (1983); Zoller, DNA 3(6):479–488 (1984); and McPherson, ed., *Directed Mutagenesis: A Practical Approach*, IRL Press, Oxford (1991).

DNA encoding the protein of the invention can be isolated from different species by using SEQ ID NO:2 to prepare one or more oligonucleotide probes. The probe is labeled and used to screen a genomic or cDNA library in a suitable vector, such as phage lambda. The homology between the DNA of the IKKαΔC of the species being screened and that of mouse is taken into account in determining the conditions of hybridization. The cDNA library may be prepared from mRNA by known methods, such as those described in Gubler and Hoffman, Gene 25, 263–270 (1983). Oligonucleotide probes can be used to screen cDNA libraries from different species and tissues. The oligonucleotide probe should be labeled so that it can be detected upon hybridization to DNA in the library being screened. These methods are well known in the art.

The DNA isolated is sequenced, and the sequence used to prepare additional oligonucleotide probes. This procedure may be repeated to obtain overlapping fragments until a complete open reading frame is produced.

The nucleic acids of the invention may be amplified by methods known in the art. One suitable method is the polymerase chain reaction (PCR) method described by Saiki et al., Science 239:487 (1988), Mullis et al in U.S. Pat. No. 4,683,195 and by Sambrook et al. (1989). It is convenient to amplify the clones in the lambda-gt10 or lambda-gt11 vectors using lambda-gt10 or lambda-gt11-specific oligomers as the amplimers (available from Clontech, Palo Alto, Calif.). Other amplification procedures that are well known in the art such as ligase chain reaction (LCR), Repair Chain Reaction (RCR), and PCR oligonucleotide ligation assay (PCR-OLA) can also be used to amplify the nucleic acids of the invention.

DNA encoding the proteins of the invention, or unique fragments thereof, may also be cloned in a suitable host cell and expressed by methods well known in the art. The DNA and protein may be recovered from the host cell. See, generally, Sambrook et al. (1989), for methods relating to the manufacture and manipulation of nucleic acids. The entire gene or additional fragments of the gene can be isolated by using the known DNA sequence or a fragment thereof as a probe. To do so, restriction fragments from a genomic or cDNA library may be identified by Southern hybridization using labeled oligonucleotide probes derived from SEQ ID NO:2.

The amplified or cloned DNA can be expressed in a suitable expression vector by methods known in the art. See, generally, Sambrook et al. (1989).

A variety of expression vectors and host cell systems can be used. These include, for example, microorganisms such as bacteria transformed with recombinant bacteriophage DNA, plasmid DNA, or cosmid DNA containing the IKKαΔC coding region. Other expression vectors and host cell systems that can be used include yeast transformed with recombinant yeast expression vectors containing the IKKαΔC coding sequence, insect cells infected with recombinant virus expression vectors containing the IKKαΔC coding sequence, plant cells infected with recombinant virus expression vectors containing the IKKαΔC coding sequence, or animal cells infected with recombinant virus expression vectors (e.g., retroviruses, adenovirus, vaccinia virus) containing the IKKαΔC coding sequence.

The expression vectors useful in the present invention contain at least one expression control sequence that is operatively linked to the DNA sequence or fragment to be expressed. The control sequence is inserted in the vector in order to control and to regulate the expression of the cloned DNA sequence. Examples of useful expression control sequences are the lac system, the trp system, the tac system, the trc system, major operator and promoter regions of phage lambda, the control region of fd coat protein, the glycolytic promoters of yeast, e.g., the promoter for 3-phosphoglycerate kinase, the promoters of yeast acid phosphatase, e.g., Pho5, the promoters of the yeast alpha-mating factors, and promoters derived from polyoma, adenovirus, retrovirus, and simian virus, e.g., the early and late promoters or SV40, and other sequences known to control the expression of genes of prokaryotic or eukaryotic cells and their viruses or combinations thereof.

Useful expression hosts include well-known prokaryotic and eukaryotic cells. Some suitable prokaryotic hosts include, for example, *E. coli*, such as *E. coli* SG-936, *E. coli* HB 101, *E. coil* W3110, *E. coil* X1776, *E. coli* X2282, *E. coli* DHI, and *E. coli* MRC1, Pseudomonas sp., Bacillus sp., such as *B. subtilis,* and Streptomyces sp. Suitable eukaryotic cells include yeasts and other fungi, insect, animal cells, such as COS cells and CHO cells, human cells and plant cells in tissue culture.

Preferably, IKKαΔC is expressed using baculoviral vectors in insect cells. In general, the transformation of insect cells and production of foreign proteins therein is disclosed in Guarino et al., U.S. Pat. No. 5,162,222.

Proteins can be isolated from a solubilized fraction by standard methods. Some suitable methods include precipitation and liquid chromatographic protocols such as ion exchange, hydrophobic interaction, and gel filtration. See, for example, *Methods Enzymol* (*Guide to Protein Chemistry*, Deutscher, ed., Section VII) pp. 182:309 (1990) and Scopes, *Protein Purification,* Springer-Verlag, New York (1987), which are herein incorporated by reference.

Alternatively, purified material is obtained by separating the protein on preparative SDS-PAGE gels, slicing out the band of interest and electroeluting the protein from the polyacrylamide matrix by methods known in the art. The detergent SDS is removed from the protein by known methods, such as by dialysis or the use of a suitable column, such as the Extracti-Gel column from Pierce. Mixtures of proteins can be separated by, for example, SDS-PAGE in accordance with the method of Laemmli, Nature 227:680–685 (1970). Such methods are well known in the art.

The proteins of the invention can also be chemically synthesized by methods known in the art. Suitable methods for synthesizing proteins are described by Stuart and Young, *Solid Phase Peptide Synthesis,* 2d ed., Pierce Chemical Company (1984).

The invention also includes an antibody or antibody fragment that specifically binds to an epitope of the proteins of the invention defined by the amino acid sequence set forth in SEQ ID NO:3 (GKTLQSQY). Also included in the invention are antibodies that bind to epitopes found on IKKαΔC that differ from IKKα and IKKβ due to differences in the protein structure because of the lack of a helix-loop-helix region. An "antibody" in accordance with the present specification is defined broadly as a protein that binds specifically to an epitope. The antibodies of the invention can be monoclonal antibodies, polyclonal antibodies, chimerized antibodies, humanized antibodies, single chain antibodies, or a fragment. For use in in vivo applications with human subjects, the antibody is preferably chimerized or humanized, containing an antigen binding region from, e.g., a rodent, with the bulk of the antibody replaced with sequences derived from human immunoglobulin.

Antibodies further include recombinant polyclonal or monoclonal Fab fragments prepared in accordance with the method of Huse et al., Science 246:1275–1281 (1989).

Polyclonal antibodies are isolated from mammals that have been inoculated with the protein or a functional analog in accordance with methods known in the art. Briefly, polyclonal antibodies may be produced by injecting a host mammal, such as a rabbit, mouse, rat, or goat, with the protein or a fragment thereof capable of producing antibodies that distinguish between mutant and wild-type protein. The peptide or peptide fragment injected may contain the wild-type sequence or the mutant sequence. Sera from the mammal are extracted and screened to obtain polyclonal antibodies that are specific to the peptide or peptide fragment.

The antibodies are preferably monoclonal. Monoclonal antibodies may be produced by methods known in the art. These methods include the immunological method described by Kohler and Milstein, Nature 256:495–497 (1975) and by Campbell, in Burdon et al., eds, *Laboratory Techniques in Biochemistry and Molecular Biology,* Vol. 13, Elsevier Science Publishers, Amsterdam (1985); as well as the recombinant DNA method described by Huse et al., Science 246:1275–1281 (1989).

To produce monoclonal antibodies, a host mammal is inoculated with a peptide or peptide fragment as described above, and then boosted. Spleens are collected from inoculated mammals a few days after the final boost. Cell suspensions from the spleens are fused with a tumor cell in accordance with the general method described by Kohler and Milstein (1975). See also Campbell (1985). To be useful, a peptide fragment must contain sufficient amino acid residues to define the epitope of the molecule being detected.

If the fragment is too short to be immunogenic, it may be conjugated to a carrier molecule. Some suitable carrier molecules include keyhole limpet hemocyanin and bovine serum albumin. Conjugation may be carried out by methods known in the art. One such method is to combine a cysteine residue of the fragment with a cysteine residue on the carrier molecule.

Methods for making chimeric and humanized antibodies are also known in the art. For example, antibodies can be engineered using genetic techniques to produce chimeric antibodies including protein components from two or more species.

For example, methods for making chimeric antibodies include those described in U.S. patents by Boss (Celltech) and by Cabilly (Genentech). See U.S. Pat. Nos. 4,816,397 and 4,816,567, respectively. Methods for making humanized antibodies are described, for example, in Winter, U.S. Pat. No. 5,225,539, Co et al., Nature 351, 501–502 (1992); Queen et al., Proc. Natl. Acad. Sci. 86, 10029–1003 (1989) and Rodrigues et al., Int. J. Cancer, Supplement 7, 45–50 (1992).

Methods are also known for inducing expression of engineered antibodies in various cell types, such as mammalian and microbial cell types. Numerous techniques for preparing engineered antibodies are described, for example, in Owens and Young, "The genetic engineering of monoclonal antibodies," J. Immunol. Meth. 168:149–165 (1994).

Methods for making single chain antibodies are also known in the art. Some suitable examples include those described by Wels et al. in European patent application 502 812 and Int. J. Cancer 60, 137–144 (1995).

Assays for directly detecting the presence of IKKα∆C with antibodies follow known formats, such as, fluorescent activated flow cytometry, fluorescent microscopy, and immuno-electron microscopy. Moreover, assays for detecting the presence of proteins with antibodies have been previously described and follow known formats, such as standard blot and ELISA formats. These formats are normally based on incubating an antibody with a sample suspected of containing the protein and detecting the presence of a complex between the antibody and the protein. The antibody is labeled either before, during, or after the incubation step. The protein is preferably immobilized prior to detection. Immobilization may be accomplished by directly binding the protein to a solid surface, such as a microtiter well, or by binding the protein to immobilized antibodies.

Suitable assays are known in the art, such as the standard ELISA protocol described by R. H. Kenneth, "Enzyme-linked antibody assay with cells attached to polyvinyl chloride plates" in Kenneth et al., *Monoclonal Antibodies,* Plenum Press, New York, pp. 376 et seq. (1981).

In another embodiment of the invention, the invention includes methods for screening for agents that modulate IκB phosphorylation by IκB kinases by screening for compounds, or agents, which modulate IκB phosphorylation by the IκB kinases of the invention, i.e. IKKα∆C. Because, unlike other IκB kinases, IKKα∆C can function as a monomer, screens for modulators of kinase activity can be targeted to a minimal IKKα functional domain. Also, because IKKβ is not required for the functional activity of the proteins of the invention, only one kinase needs to be present in the kinase assay. These are unique advantages provided by the invention that simplify the analysis and search for modulating agents that are useful therapeutics.

Modulation of IκB phosphorylation can be either inhibition or an increase in phosphorylation (induction) at an IκB phosphorylation site. Therefore, modulating agents are either inhibitors or inducers of IκB phosphorylation by IκB kinases. Inhibitors are useful as immunosuppressants or antiinflammatory agents. Inducers can be used, for example, to stimulate immune responses in immunosupressed patients.

Screening for agents that modulate IκB phosphorylation by IKKα∆C comprises the steps of incubating a mixture of IKKα∆C, an IκB phosphorylation site, and a candidate modulating agent and detecting the agent-biased phosphorylation level of the phosphorylation site by the kinase. The agent-biased phosphorylation level is then compared with an agent-independent phosphorylation level determined in the absence of the modulating agent. In this way, candidate modulating agents can be identified and assessed for their potential effectiveness as therapeutic agents. A significant difference between the agent-biased phosphorylation level and the agent-independent phosphorylation level indicates that the agent modulates IκB phosphorylation. A difference, as used herein, is a significant difference, where preferably at least 10% difference is observed, more preferably at least 50%, and most preferably, at least 80%. An agent that modulates IκB phosphorylation by IκB kinases can be used, or developed, for therapeutic purposes.

Candidate modulating agents can be selected from small molecules, peptides, and proteins. Small molecules are desirable as therapeutic agents since they are more likely to be permeable to cells and are less susceptible to degradation than are biological macromolecules. Small molecules include, but are not limited to, organic or inorganic compounds of molecular weight less than 700 and peptides of molecular weight less than 10 kDa. The organic or inorganic compounds can be synthetic or natural. Proteins, such as antibodies, and peptides having a molecular weight greater than 10 kDa can also be candidate modulating agents. The methods of the invention are amenable to high-throughput screening of chemical libraries and are especially useful for identifying small molecule drug candidates.

IκB phosphorylation sites include the serine residues of IκBs that are phosphorylated by IκB kinases. In the case of IκBα, the phosphorylation sites include serine 32 and/or serine 36. However, other IκB phosphorylation sites such as serine 19 and/or serine 23 of IκBβ can also be used. In addition, other IκB phosphorylation sites present on different variants of IκB, alleles of IκB, and fragments of IκB proteins that maintain the structural integrity of IκB phosphorylation sites, can be used.

The agent-biased phosphorylation level is the phosphorylation observed in the presence of a candidate modulating agent and the agent-independent phosphorylation level is the phosphorylation level in the absence of the candidate modulating agent.

The assay mixture can additionally comprise a variety of other components such as salts, buffers, carrier proteins (e.g. albumin), detergents, protease inhibitors, etc., that may be used to improve the efficiency of the assay.

Any phosphorylation assay (kinase assay) known in the art can be used with this embodiment of the invention. For example, the phosphorylation assays described in U.S. Pat. No. 5,776,717 to Cao, with appropriate modifications, can be used. U.S. Pat. No. 5,776,717 to Cao is herein incorporated by reference for its kinase assay disclosure. A preferred kinase assay uses GST-fusion proteins of appropriate IκB substrates. GST-fusions are described in Smith and Johnson, Gene 67, 31–40 (1988).

EXAMPLES

Abbreviations

AKAP, A-kinase anchoring protein; CHUK, conserved helix-loop-helix ubiquitous kinase; GST, glutathione S-transferase; HA, hemagglutinin; IKK, IκB kinase; IL, Interleukin; MEKK-1, mitogen-activated protein kinase/ERK kinase kinase-1; NIK, NF-κB-inducing kinase; RT, reverse transcriptase; TNF, tumor necrosis factor: TRAF, tumor necrosis factor receptor-associated factor.

Materials and Methods cDNA Clones and Plasmid Constructions

IKKαΔC was isolated from a normal BXSB mouse spleen cDNA library by screening with a DNA probe containing portions of the IKKα amino proximal kinase and leucine zipper domains. IKKα and IKKαΔC were subsequently cloned into the pcDNA3.1 (Invitrogen) expression vector in frame with a C-terminal hemaglutinin (HA) epitope tag by PCR. IKKα-(K44A)-HA, GST-IκB(1–62) and GST-IκB (1–62)(SS32,36AA) were also generated by PCR. See Geleziunas et al. Mol. Cell. Biol. 18, 5157–5165 (1998). The NF-κB dependent luciferase reporter plasmid (κB-TATA luciferase) has been previously described. Sun et al., Mol. Cell. Biol. 16, 1058–1065 (1996).

Antibodies

Rabbit polyclonal antibodies directed against native IKKα (Sc-H744) were purchased from Santa Cruz Biotechnology Inc. (Santa Cruz, Calif. Rabbit polyclonal antiserum NR-1997 was raised against the synthetic peptide RPPGLRPGAGGPWEMRER, corresponding to aminoacids 3–20 of CHUK/IKKα (100% conserved between mouse and human IKKα). Anti-Flag tag antibodies (M2) were purchased from Eastman Kodak Company (Hollywood, Calif.). Anti-HA tag mouse monoclonal antibody 12CA5 was obtained from Berkeley Antibody Company (Richmond, Calif.)

Cells and Culture Conditions

Human Embryonic Kidney cells (HEK 293) and HeLa cells were cultivated in Dulbecco's modified Eagle's medium (DMEM, from Gibco/BRL) containing either 10% fetal bovine serum or 10% calf serum respectively supplemented with penicillin (50 U/ml) and streptomycin sulfate (50 μg/ml).

Luciferase Reporter Assays 293 cells were seeded in 6-well plates at a density of $6 \times 10^5$ cells per well the day before transfection. DNA transfections were performed by the calcium phosphate precipitation method with up to 4 μg of expression plasmid, 0.5 μg of NF-κB luciferase reporter plasmid and 0.25 μg of RSV-βGal plasmid which served as an internal transfection efficiency control. Total DNA concentrations in each transfection were kept constant by supplementing with empty pcDNA3.1 expression vector. Twenty four hours post-transfection, cells were stimulated where appropriate with TNFα (10 ng/ml) for 6 h prior to cell lysis. Luciferase and β-Galactosidase activities were quantitated with a Promega Inc. (Madison, Wis.) assay kit as recommended by the provider.

RT-PCR

Total poly A+ RNAs from various cell lines and tissues were reverse transcribed into cDNAs in a 20 μl reverse transcriptase reaction containing 50 mM Tris-HCl (pH 8.3), 40 mM KCl, 6 mM MgCl$_2$, 1 mM of each of dNTP, 200 units of mouse mammary tumor RT, 12 units of RNAsin (Promega), 2 μg of poly A+RNA and 40 pmol of oligoT primer incubated at 37° C. for 45 min. For the PCR reaction, volumes were increased to 100 μl in 10 mM Tris-HCl (pH 8.3), 50 mM KCl, 1.5 mM MgCl$_2$, 0.001% gelatin, 0.4 mM of the following primers to selectively amplify IKKα (CHUK) and IKKαΔC (5' primer: 5'-ACCATTTGCATCCAGAAGTTTATC-3'; IKKα (CHUK) specific 3'primer: 5'-TGCAAAAAGAATACCAAAACAGGAT-3'; IKKαΔC specific 3' primer: 5'-CCATCTCTGTGCTGTCGCTGTA-3') and 5 units of Taq polymerase (Perkin-Elmer/Cetus corp.). Amplification conditions were 5 cycles (1 min at 95° C., 1 min at 37° C. and 2 min at 72° C.) followed by 50 cycles (1 min at 95° C., 1 min at 55° C. and 2 min at 72° C.). The reaction products were resolved on a 6% polyacrylamide gel.

Western Blot Analysis

Cells were washed twice with cold PBS and lysed in Triton X-100 lysis buffer (50 mM Tris-HCl, pH 7.5, 100 mM NaCl, 50 mM NaF, 5 mM EDTA, 40 mM β-glycerophosphate, 200 μM sodium orthovanadate, $10^{-4}$ M phenylmethyl-sulfonyl fluoride, 1 mg/ml leupeptin, 1 μM pepstatin A, 1% Triton X-100) for 15 minutes at 4° C. Insoluble material was removed by centrifugation at 12000×g for 2 min at 4° C. Proteins from cell lysates (100 μg) were separated on 7.5% SDS-PAGE and electrophoretically transferred to Hybond-C Extra membranes (Amersham) in 25 mM Tris-HCl, 0.19 M glycine. Membranes were blocked in TBS (25 mM Tris-HCl, pH 7.5, 137 mM NaCl) containing 5% non fat dry milk. The blots were then incubated with antisera in blocking solution for 2 hours at room temperature. After washing in TBS, 0.1% Triton X-100, blots were incubated with horseradish peroxidase-conjugated goat anti-rabbit IgG or goat anti-mouse IgG as appropriate (1:3000) in blocking solution for 1 h and revealed with an ECL immunodetection kit (Amersham Corporation, Arlington Heights, Ill.).

Immune Complex Kinase Assays

For IKKα/IKKαΔC, 293 cells were seeded in 10 cm plates (2.5×106 cells per plate) and transfected the next day with 10 μg of kinase expression plasmid by the calcium phosphate precipitation method. Twenty four hours later the cells were stimulated in DMEM with the appropriate agonist at 37° C. for the times indicated, washed with ice cold PBS and lysed with Triton X-100 lysis buffer as described for western blot analysis. Proteins from lysates (500 μg) were incubated with specific anti-HA 12CA5 antibodies pre-adsorbed to protein A-Sepharose coated beads for 2 h at 4° C. Immune complexes were washed three times with Triton X-100 lysis buffer and twice with kinase buffer (10 mM HEPES, pH 7.4, 20 mM MgCl$_2$, 1 mM dithiothreitol, 10 mM p-nitrophenylphosphate). IKKα (CHUK) activity was assayed by resuspending the final pellet in 40 μl of kinase buffer containing 50 μM of [γ-$^{32}$P] ATP (5000 cpm/pmol) (Amersham) and 0.25 mg/ml of GST-IκBα(1–62). The reaction was incubated for 10 min at 30° C. and stopped by addition of Laemmli sample buffer. Samples were resolved on SDS-PAGE (10%) and phosphorylation determined following exposure in a phosphorimager (Fuji or Molecular Dynamics)

In-vitro Translation

Constructs in pcDNA3.1 were translated in a Promega rabbit reticulocyte in-vitro translation kit either with $^{35}$S-methionine (Amersham) or with unlabeled methionine as per the manufacturer's instructions.

Sucrose Density Gradients

Sucrose gradients (20%–5%) were prepared by manual layering of sucrose solutions in a stepwise manner (500 μl per step) to a total volume of 3.5 ml in 50 mM Tris/HCl, 75 mM NaCl, pH 7.5 IKKα, IKKαΔC and NIK constructs which had been translated in vitro either with $^{35}$S-methionine (Amersham) or with unlabeled methionine were incubated for 30 min at 25° C. prior to addition to the sucrose gradients in a final volume of 30 μl (~100 μg of reticulocyte protein). In separate, identically prepared tubes, standards were added (5 μg each of catalase, bovine serum albumin and ovalbumin in a total volume of 30 μl). Gradients were centrifuged in a Beckman SW56.1 rotor at 50,000 rpm for 10 h at 25° C. Gradients were fractionated (from the bottom) into 15x~250 μl fractions and 100 μl of each fraction was resolved by SDS-PAGE (7.5%). Following fixing in 10% methanol/10% acetic acid, gels were incubated in Amplify (Amersham) for 30 min., prior to drying and exposure in a Fuji phosphorimager. Images were densitometrically scanned and quantified. In control gradients, fractions were isolated and proteins resolved on identical SDS-PAGE, however, the gels were stained with coomassie blue (0.1%(w/v) in 40% methanol, 10% acetic acid) to reveal the protein standards and scanned densitometrically to determine their distribution profile.

Protein Determinations

Proteins were quantitated with a bicinchoninic acid protein assay kit (Pierce, Rockford, Ill.) using bovine serum albumin as a standard.

Example 1

Cloning, Structural Features and Expression of an IKKαΔC Polypeptide

Several cDNA libraries were screened with 5' terminal IKKα (CHUK) specific DNA probes. This screening consistently revealed several structurally related IKKα cDNA clones which appeared to result from differential RNA splicing and alternative exon usage. Complete sequence analysis of one such cDNA clone from a BXSB mouse spleen cDNA library revealed it to encode an IKKα isoform (denoted IKKαΔC) (see FIG. 1). The sequences of IKKα and IKKαΔC are identical until nucleotide 1728, amino acid 576 (89 residues 3' of the leucine zipper domain) where they diverge just 8 amino acids prior to the carboxy-proximal H-L-H domain. IKKαΔC also possesses a unique 8 amino acid C-terminal tail and a novel 3' non-coding sequence. The structure of the IKKαΔC 3' non-coding sequence reveals that it possesses significant homology to the sequence of the H-L-H domain suggesting that it may be specified by a duplicated, divergent exon (see FIG. 1B). IKKαΔC is a truncated IKKα molecule with a calculated molecular mass of 60 kDa. Sequence analyses of RT-PCR products obtained with IKKα and IKKαΔC specific 3' primers revealed that both forms of IKKα are ubiquitously expressed in a variety of cell lines and normal tissues.

Example 2

Expression of Transfected and Endogenous IKKαΔC

To determine if cells co-expressed IKKα and IKKαΔC polypeptides, immunoblotting experiments were undertaken with a variety of IKKα specific antisera. The specificity of each anti-sera for either IKKα or IKKαΔC was rigorously determined with lysates of 293 cells transiently transfected with expression vectors producing either HA epitope tagged IKKα or IKKαΔC. Each recombinant protein was also produced by in vitro cell-free translation which served as additional standards verifying antisera specificities.

In vitro translated IKKα and IKKαΔC were immunoprecipitated with antiserum SC-H744, NR-1997 or normal rabbit serum (con). Immnunoprecipitates were resolved on SDS-PAGE (8% gels) and the presence of IKKα and IKKαΔC was revealed following exposure in a phosphorimager. 293 cells were transiently transfected with plasmids encoding HA-epitope tagged IKKα and IKKαΔC sequences. Cell lysates (100 μg protein) were resolved on SDS-PAGE, transferred to nitrocellulose and western blotted with antiserum NR-1997.

These analyses revealed that an IKKα-directed polyclonal antisera (ScH744) purchased from Santa Cruz Biotechnology Inc. (Santa Cruz, Calif.) only detected the larger IKKα isoform following western blotting or in immunoprecipitation experiments.

In contrast, another rabbit polyclonal Ab raised against an N-terminal IKKα/IKKαΔC, although capable of immunoprecipitating both IKKα and IKKαΔC and detecting transfected IKKα and IKKαΔC in transient overexpression assays, preferentially detected the smaller IKKαΔC isoform in western bots of HeLa cell extracts. Endogenous IKKα proteins in 293 cells were barely detectable in most westerns while similar levels of IKKα and IKKαΔC polypeptides were expressed by HeLa cells.

Example 3

IKKαΔC Upregulates NF-κB Dependent Gene Transcription

Activation of NF-κB in response to a variety of agonists is readily detectable in transient transfection assays using an NF-κB-dependent reporter gene construct. It was investigated whether IKKαΔC, akin to IKKα and IKKβ, was also a cytokine responsive stimulator of NF-κB activity.

Figure 2A:
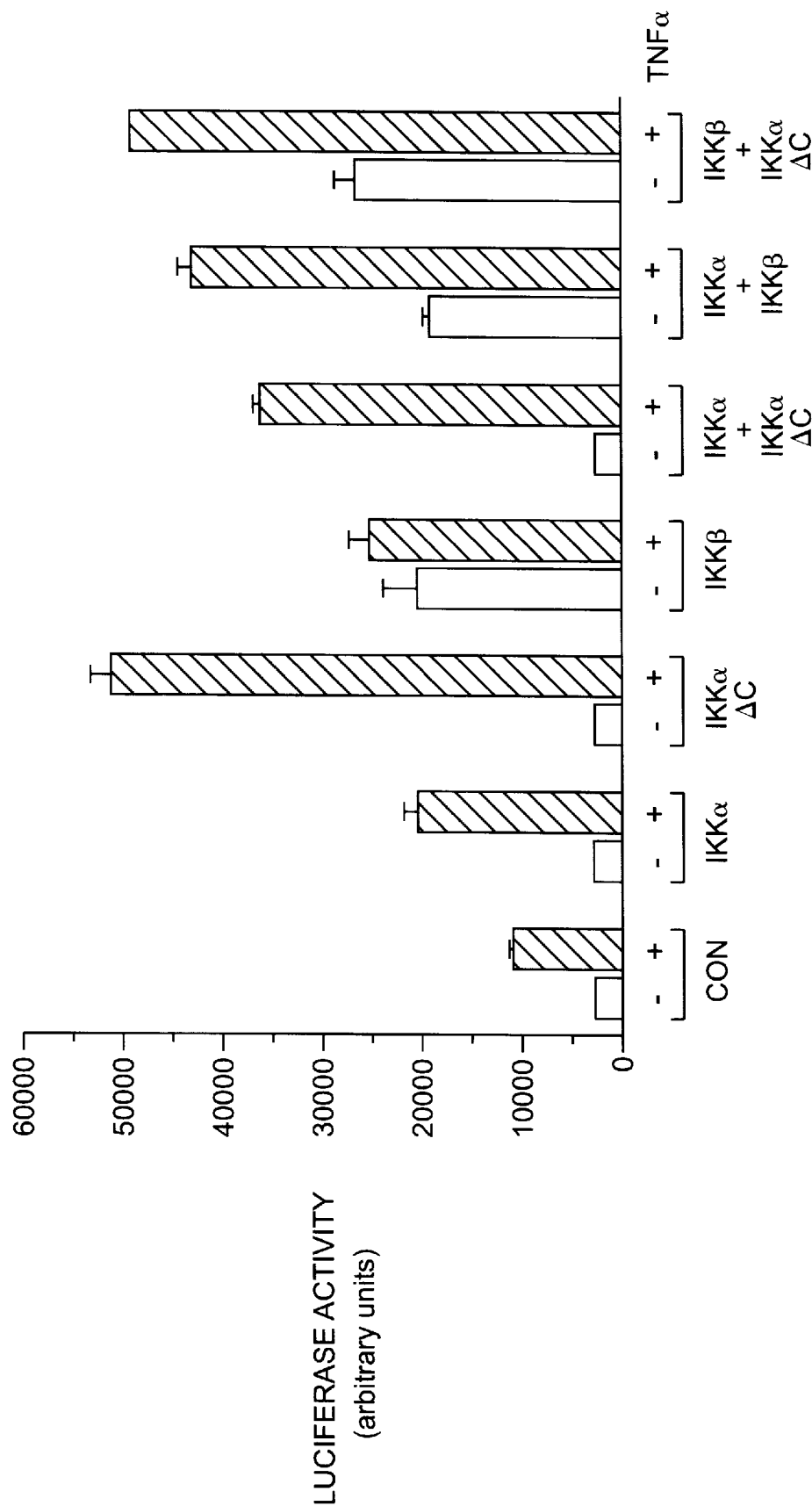
FIG. 2A is a bar graph showing the activation of NF-κB by IKKαΔC and other IκB kinases.

293 cells were transiently transfected with plasmids encoding IKKα, IKKαΔC or IKKβ as indicated in FIG. 2A, either separately or in combination, together with reporter plasmid (NF-κB-luciferase). Twenty four hours after transfection, cells were stimulated or not for 6 h with TNFα (10 ng/ml) prior to cells lysis and luciferase activity measurement as described above.

Co-transfection of IKKα produced a slight increase in basal NF-κB-driven luciferase activity and a strong increase in TNFα-stimulated luciferase activity. Unexpectedly, as shown in FIG. 2A, IKKαΔC was found to be even more potent than IKKα in the same assay. In contrast to both IKKα and IKKαΔC, IKKβ was constitutively active and enhanced the activity of the NF-κB driven luciferase reporter independent of cytokine stimulation in agreement with other reports. See, for example, Mercurio et al., Science 278, 860–866 (1997). However, the maximal activity provided by IKKβ was less than that obtained by co-transfection of either IKKα or IKKαΔC in conjunction with TNFα stimulation.

It was previously reported that IKKα and IKKβ co-immunoprecipitate and appear to function as a heterodimer (Mercurio et al., Science 278, 860–866 (1997); Woronicz et al.,Science 278, 866–869 (1997); Zandi, E. et al., Cell 91, 243–252 (1997). The effects of each kinase alone and in pairwise combinations on the cytokine dependent induction of NF-κB activity in 293 cells were compared (see FIG. 2A). Again, IKKβ was found to dominate the response in that its inclusion induced luciferase activity in the absence of agonist stimulation. Nevertheless, the inclusion of either IKKα or IKKαΔC in co-transfections always led to an increase in TNFα-stimulated luciferase activity which was similar to that elicited when either IKKα or IKKαΔC were expressed alone.

Since these experiments suggested that IKKαΔC might be a more effective activator of NF-κB dependent gene induction than IKKα, dose-response studies were undertaken wherein 293 cells were transiently transfected with a constant amount of NF-κB reporter plasmid along with increasing amounts of plasmids expressing either IKKα or IKKαΔC.

293 cells were transiently transfected with increasing amounts of plasmid encoding HA-IKKα or HA-IKKαΔC together with reporter plasmid (NF-κB-luciferase). Twenty four hours after transfection, cells were stimulated for 6 h with TNFα (10 ng/ml) prior to cell lysis and luciferase activity measurement. A western blot analysis of HA-IKKα or HA-IKKαΔC protein expression in lysates (100 μg protein) from cells transfected with 1 and 5 mg of each plasmid was also conducted.

Figure 2B:
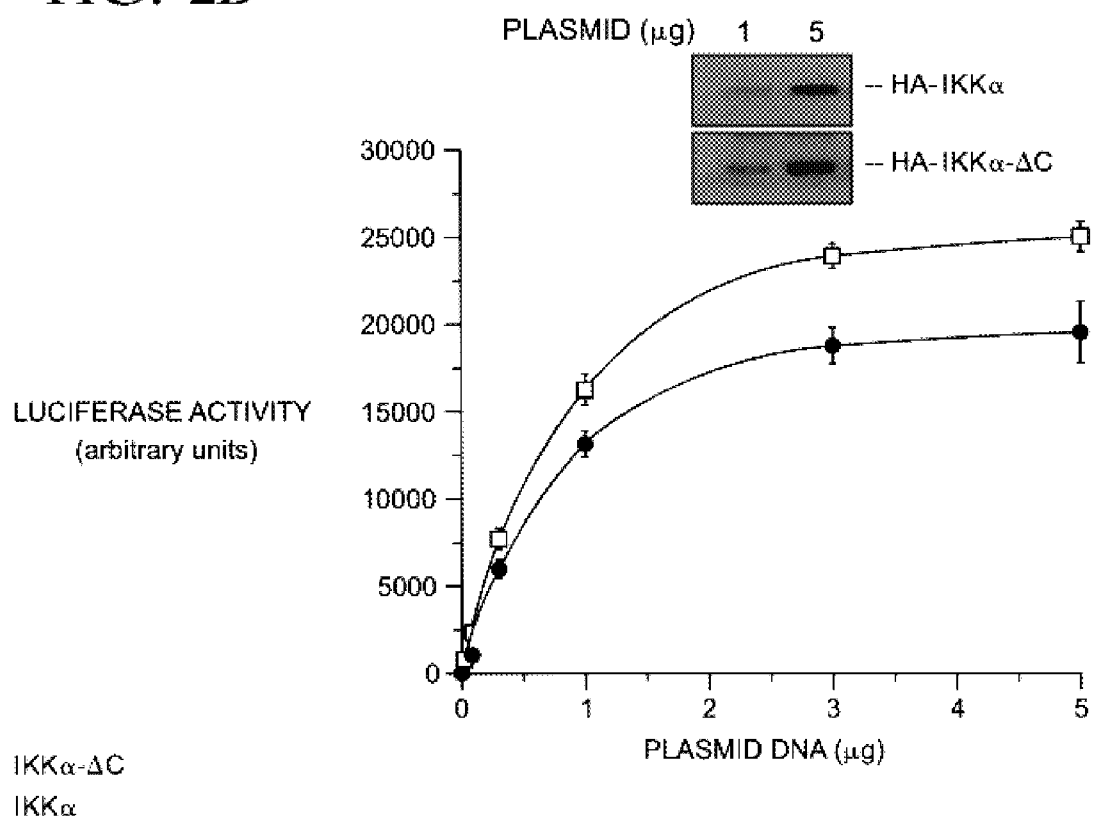
FIG. 2B shows the activation of NFκB with increasing amounts of either IKKα or IKKαΔC.

As shown in FIG. 2B, as the amount of plasmid encoding either IKKα or IKKαΔC was increased, the TNFα-induced luciferase activity increased correspondingly, although the increase was more marked for IKKαΔC. The Western blot experiments on lysates of 293 cells transfected with either 1 or 5 μg of IKKα or IKKαΔC encoding plasmids revealed similar levels of protein expression. Hence, in comparison to IKKα, IKKαΔC is somewhat more efficient at inducing NF-κB in response to TNFα.

The cascade of cytoplasmic proteins leading from receptors, such as those for TNFα, to phosphorylation of IκB requires both NIK and IKK. Malinin et al., Nature 385, 540–544 (1997). Thus, catalytically inactive mutant forms of either kinase attenuate TNFα-mediated activation of NF-κB. If IKKαΔC shares a common activator with IKKα, then we might expect a catalytically inactive mutant of IKKα to act as a 'sink' and titrate out the ability of an upstream activator to stimulate IKKαΔC. This hypothesis was tested by transiently transfecting 293 cells with the NF-κB-dependent reporter construct, either IKKα or IKKαΔC and increasing concentrations of plasmid encoding IKKα (K44A), a catalytically inactive form of IKKα.

Figure 2C:
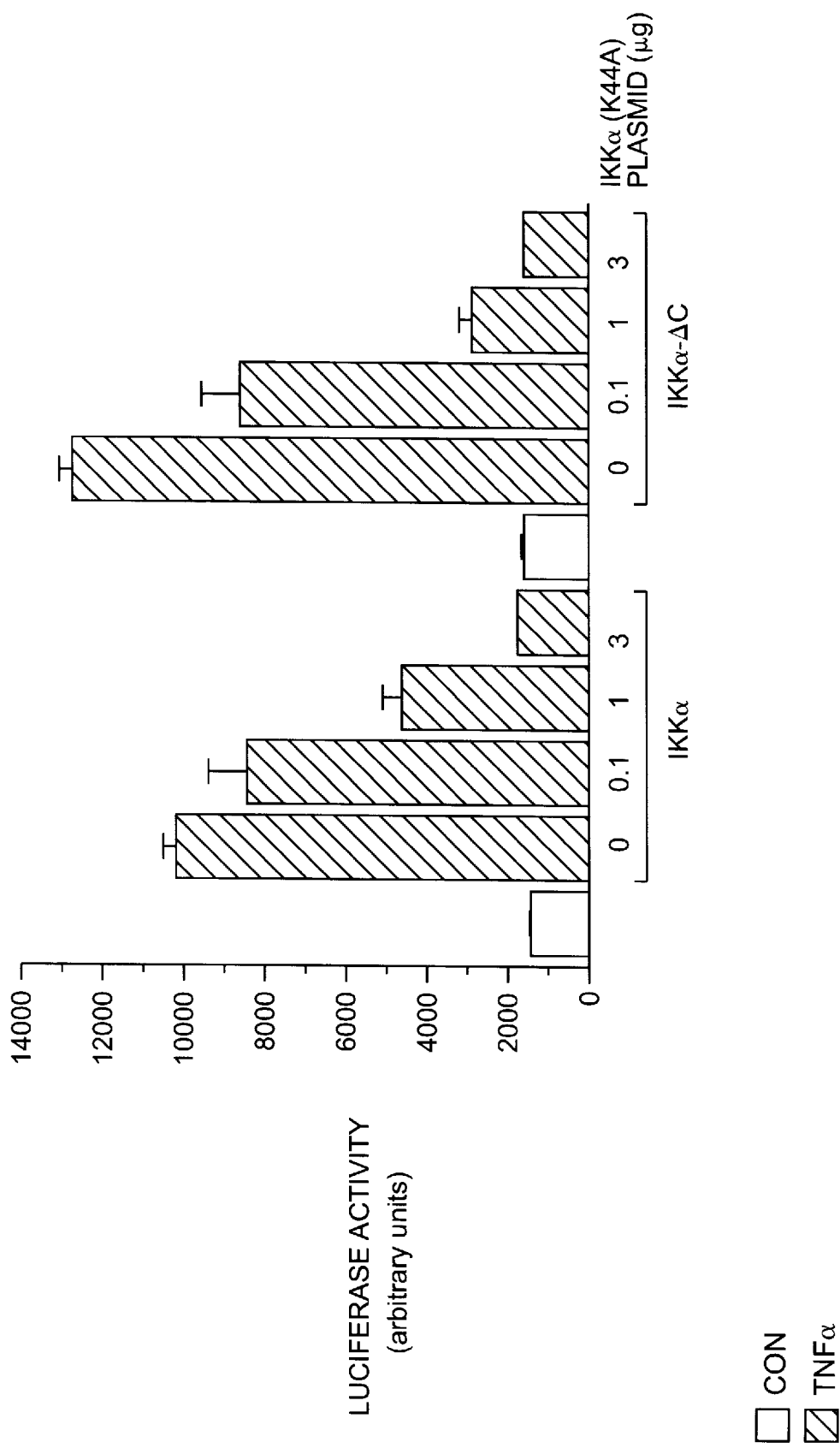
FIG. 2C shows that increasing concentrations of a dominant negative catalytically inactive form of IKKα, IKKα-K44A, elicit a dose-dependent reduction in the ability of IKKα or IKKαΔC to support TNFα-mediated activation of NFκB.

293 cells were transiently transfected with plasmid encoding IKKα or IKKαΔC (μg per well) together with reporter plasmid (NF-κB luciferase, 0.5 μg per well) and increasing concentrations of plasmid encoding catalytically inactive IKKα, IKKα (K44A). Twenty four hours after transfection, cells were stimulated or not for 6 h with TNFα (10 ng/ml) prior to cell lysis and luciferase activity measurement. In FIG. 2C luciferase activity is expressed as arbitrary units normalised to β-galactosidase activity. Data are means±range of duplicate determinations from a single experiment representative of three such performed.

FIG. 2C shows that increasing concentrations of IKKα (K44A) elicit a dose-dependent reduction in the ability of both IKKα and IKKαΔC to support the TNFα-mediated activation of the NF-κB reporter construct. Hence, IKKαΔC may participate in the same pathway as IKKα to activate NF-κB.

Example 4
IKKαΔC is a Functional NF-κB Kinase

Release of NF-κB from its IκBα inhibitor requires the latters phosphorylation at amino terminal serines 32 and 36. Lin et al., Proc. Natl. Acad. Sci U.S.A. 92:552–556 (1995). To assess the relative abilities of IKKα and IKKαΔC to phosphorylate IκBα in response to cytokine stimulation, in vitro kinase assays were performed with GST-IκB (1–62) as substrate in anti-HA immunoprecipitates of 293 cells transfected with HA-epitope tagged IKKα and IKKαΔC.

293 cells were transiently transfected with plasmids encoding HA-IKKα or HA-IKKαΔC. Twenty four hours post-transfection, cells were stimulated or not for 5 min with TNFα (10 ng/ml) prior to cell lysis. HA-IKK immunoprecipitation and determination of IKK activity were performed as described above. In parallel transfections, western blots were performed using anti-HA antibodies to verify the protein expression levels of HA-IKKα and HA-IKKαΔC.

293 cells transiently transfected with either IKKα and IKKαΔC expressed similar amounts of immunodetectable proteins with the expected molecular mass. Stimulation of both IKKα and IKKαΔC transfected 293 cells with TNFα resulted in an increase in immunoprecipitatable kinase activity towards GST-IκB(1–62).

In time course experiments shown in FIG. 3, the activation profiles of IKKα and IKKαΔC in response to TNFα stimulation were found to be superimposable. 293 cells were transiently transfected with plasmid encoding HA-IKKα or HA-IKKαΔC. Twenty fours hours after transfection, cells were stimulated or not for the times indicated with TNFα (10 ng/ml) prior to cell lysis, HA-IKK immunoprecipitation and determination of IKK activity. Data are expressed as the fold increase in kinase activity relative to the basal activity and are means±range of single determinations pooled from three experiments. See FIG. 3. Control immune-complex kinase assays performed with a mutated GST-IκB(1–62) (serines 32 and 36 mutate to alanines) failed to support phosphorylation. Hence, like IKKα, IKKαΔC is also a cytokine stimulated IκB kinase.

Example 5
IKKαΔC is a Monomer in vitro, but Associates With NIK

IKKα and IKKαΔC possess functional domains (see FIG. 1). These functional domains are known to play a role in protein-protein association. Klemm et al., Annu. Rev. Immunol. 16, 569–592 (1988). Indeed, IKKα was identified as being a component of a high molecular weight cytoplasmic complex by several groups. Chen et al., Cell 84, 853–862 (1996); DiDonato et al., Nature 388, 548–554 (1997); Lee et al., Cell 88, 213–222 (1997). Co-transfection assays demonstrate that IKKα and IKKβ co-immunoprecipitate with themselves and each other, see Mercurio et al., Science 278, 860–866 (1997); Woronicz et al. (1997); and Zandi et al. (1997), suggesting that either the protein complex precipitates with each IKK or that IKKα and IKKβ form both homo- and hetero-dimers. Since IKKαΔC was lacking the IKK H-L-H domain, we performed sucrose-density gradient (SDG) centrifugation analysis of IKKα, IKKαΔC, and IKKβ to determine if each kinase behaved in a similar fashion.

IKKα, IKKαΔC and IKKβ were translated in vitro with either $^{35}$S-Methionine or unlabeled methionine as indicated, prior to separation by sucrose density gradient centrifugation (20–5% sucrose) as described above. Fractions were isolated and proteins resolved on SDS-PAGE (8% gels). The position and quantity of radiolabelled IKKs was determined following phosphorimager exposure. Catalase, BSA and Ovalbumin standards were visualized by coomassie blue gel staining. Where indicated, $^{35}$S-IKKαΔC was incubated with unlabeled, translated IKKα or IKKβ for 30 min at 25° C. prior to centrifugation. The results are shown in FIG. 4. Data are from single experiments performed twice and are relative quantities compared to the maximal quantity detected.

Under the experimental conditions employed, more than 90% of the IKKα was observed to migrate in SDG as a dimer or greater, with 10% of the proteins migrating as a monomeric species. See FIG. 4. Migration of SDG-resolved IKKα (CHUK) showed the protein to bind to additional proteins present in the reticulocyte lysate. This was unlikely to be due to non-specific aggregation as the presence of 4 M Urea in SDS-PAGE gels failed to modify the IKKα migration. Hence, IKKα most probably exists as a dimer or a larger oligomer. In contrast, IKKαΔC was seen to migrate in SDG as a monomeric species (>90% of the detectable protein). Furthermore, IKKαΔC failed to associate to a significant extent with either IKKα or IKKβ as the addition of either IKKα or IKKβ did not appreciably alter the migration profile of IKKαΔC in SDG. Experiments were performed at both 40° C. and 25° C. as this may affect dimerisation, with comparable results being obtained. Additional experiments revealed that IKKα and IKKβ migrated at the same relative positions in SDG, when added singly or together, suggesting that they associate in the same complex. These results show that IKKαΔC is a functional IKK but not via a direct interaction with either IKKα or IKKβ.

Example 6
IKKαΔC Associates With NIK in Vivo

IKKα was originally identified as being a NIK-binding protein in a yeast-two-hybrid screen (Malinin et al. Nature 385, 540–544 (1997)). Furthermore, deletion of the entire C-terminal tail (up to the leucine zipper) of IKKβ did not prevent association of IKKβ with its putative upstream activator NIK. Woronicz, et al. (1997). Therefore, it was examined whether IKKαΔC was able to interact with NIK. To assay for NIK-IKKαΔC binding, HA-epitope-tagged IKKαΔC and FLAG-epitope tagged NIK were produced by in vitro translation in the presence of $^{35}$S methionine. These proteins were preincubated for 15 min at 30° C. prior to selective immunoprecipitation with either anti-HA or anti-FLAG antibodies. HA-IKKαΔC and FLAG-NIK were translated in vitro with $^{35}$S-methionine and pre-incubated for 15 min at 30° C. prior to immunprecipitation with either anti-HA or anti-FLAG antibodies. Proteins from immunoprecipitates were resolved on SDS-PAGE (8% gels), dried and exposed in a phosphorimager. The results showed that IKKαΔC co-immunoprecipitates with NIK and vice-versa. Furthermore, an examination of the proportion of both HA-epitope-tagged IKKαΔC and FLAG-epitope tagged NIK which did not-coprecipitate revealed co-precipitation to occur with more than 80% of the proteins. Similar co-immunoprecipitation experiments were performed with 293 cells transiently transfected with both HA-epitope-tagged IKKαΔC and FLAG-epitope tagged NIK. Again, a reciprocal immunprecipitation experiment revealed that both HA-epitope-tagged IKKαΔC and FLAG-epitope tagged NIK co-immunoprecipitated.

What is claimed is:

1. An isolated nucleic acid molecule that encodes an IκB protein kinase αΔC having a kinase domain, a leucine zipper like α-helix domain, and no helix-loop-helix domain wherein the kinase domain and leucine zipper like domain of the protein comprise the amino acid sequence as set forth in SEQ ID NO:1.

2. An isolated nucleic acid molecule according to claim 1, wherein the kinase domain of the protein is a Serine/Threonine kinase domain.

3. An isolated nucleic acid molecule according to claim 1, that further encodes the amino acid sequence, (GKTLQSQY), as set forth in SEQ ID NO:3 at its carboxy terminal.

4. An isolated nucleic acid molecule as set forth in SEQ ID NO:2.

5. A method of making an IκB protein kinase αΔC having a kinase domain, a leucine zipper like α-helix domain, and no helix-loop-helix domain by expressing the nucleic acid molecule of claim 1.

6. A method of making an IκB protein kinase αΔC having a Serine/Threonine kinase domain, a leucine zipper like α-helix domain, and no helix-loop-helix domain by expressing the nucleic acid molecule of claim 2.

7. A method of making an IκB protein kinase αΔC by expressing the nucleic acid molecule of claim 4.

8. A method of making an IκB protein kinase αΔC having a kinase domain, a leucine zipper like α-helix domain, an amino acid sequence, (GKTLQSQY), as set forth in SEQ ID NO:3 at its carboxy terminal, and no helix-loop-helix domain by expressing the nucleic acid molecule of claim 3.

* * * * *